United States Patent
Bonutti et al.

(10) Patent No.: US 9,463,042 B2
(45) Date of Patent: Oct. 11, 2016

(54) METHODS AND SYSTEMS FOR CONTROLLING AN ULTRASONIC HANDPIECE BASED ON SENSED PRESSURE

(75) Inventors: Peter M. Bonutti, Effingham, IL (US); Justin Beyers, Effingham, IL (US); Matthew Cremens, Effingham, IL (US)

(73) Assignee: P Tech, LLC, Effingham, IL (US)

( * ) Notice: Subject to any disclaimer, the term of this patent is extended or adjusted under 35 U.S.C. 154(b) by 562 days.

(21) Appl. No.: 13/495,735

(22) Filed: Jun. 13, 2012

(65) Prior Publication Data

US 2012/0316473 A1    Dec. 13, 2012

Related U.S. Application Data

(60) Provisional application No. 61/496,147, filed on Jun. 13, 2011, provisional application No. 61/526,182, filed on Aug. 22, 2011, provisional application No. 61/526,207, filed on Aug. 22, 2011.

(51) Int. Cl.
| | |
|---|---|
| *A61B 5/05* | (2006.01) |
| *A61B 17/32* | (2006.01) |
| *A61H 1/00* | (2006.01) |
| *A61B 17/00* | (2006.01) |

(52) U.S. Cl.
CPC ............... *A61B 17/320068* (2013.01); *A61B 2017/00022* (2013.01); *A61B 2090/064* (2016.02)

(58) Field of Classification Search
CPC ........... B06B 1/00; B06B 3/00; G10K 11/00; A61B 2017/00106
USPC .................... 600/437, 438, 336, 459; 601/2; 73/584–648; 367/87
See application file for complete search history.

(56) References Cited

U.S. PATENT DOCUMENTS

| | | | |
|---|---|---|---|
| 4,027,559 A | | 6/1977 | Wallrafen |
| 4,651,716 A | | 3/1987 | Forester et al. |
| 4,750,902 A | | 6/1988 | Wuchinich et al. |
| 5,242,385 A | | 9/1993 | Strukel |
| 5,391,144 A | | 2/1995 | Sakurai et al. |
| 5,514,086 A | | 5/1996 | Parisi et al. |
| 5,674,235 A | | 10/1997 | Parisi |
| 5,796,007 A | | 8/1998 | Panagotopulos et al. |
| 5,897,569 A | | 4/1999 | Kellogg et al. |
| 5,938,677 A | * | 8/1999 | Boukhny et al. ............. 606/169 |

(Continued)

OTHER PUBLICATIONS

Non-Final Office Action dated Jan. 5, 2015 relating to U.S. Appl. No. 13/495,728, 21 pages.

(Continued)

*Primary Examiner* — Tse Chen
*Assistant Examiner* — Joanne Hoffman
(74) *Attorney, Agent, or Firm* — Senniger Powers LLP

(57) ABSTRACT

A system includes a handpiece configured to generate vibratory energy, and a generator coupled to the handpiece. The generator includes a processing device and a memory device having encoded thereon computer-readable instructions that are executable by the processing device to perform functions including receiving a pressure signal from the handpiece. The pressure signal is indicative of a pressure between the handpiece and a surgical implement. The functions further include determining the pressure between the handpiece and the surgical implement, comparing the pressure to a predetermined pressure range, and transmitting a control signal to the handpiece when the pressure is within the predetermined pressure range.

17 Claims, 4 Drawing Sheets

(56) References Cited

U.S. PATENT DOCUMENTS

| | | | |
|---|---|---|---|
| 5,968,060 A | 10/1999 | Kellogg | |
| 5,997,533 A | 12/1999 | Kuhns | |
| 6,017,354 A | 1/2000 | Culp et al. | |
| 6,028,387 A | 2/2000 | Boukhny | |
| 6,053,906 A | 4/2000 | Honda et al. | |
| 6,217,591 B1* | 4/2001 | Egan et al. | 606/144 |
| 6,352,532 B1 | 3/2002 | Kramer et al. | |
| 6,425,865 B1 | 7/2002 | Salcudean et al. | |
| 6,475,215 B1* | 11/2002 | Tanrisever | H05H 1/24 606/32 |
| 6,494,095 B1 | 12/2002 | Wan | |
| 6,602,193 B2 | 8/2003 | Chon | |
| 6,678,621 B2 | 1/2004 | Wiener et al. | |
| 6,679,899 B2 | 1/2004 | Wiener et al. | |
| 6,817,973 B2 | 11/2004 | Merril et al. | |
| 7,063,692 B2* | 6/2006 | Sakurai | A61B 17/320068 600/101 |
| 7,235,072 B2 | 6/2007 | Sartor et al. | |
| 7,273,483 B2 | 9/2007 | Wiener et al. | |
| 7,313,949 B2 | 1/2008 | Yorita et al. | |
| 7,476,233 B1 | 1/2009 | Wiener et al. | |
| 7,758,547 B2 | 7/2010 | Tonelli et al. | |
| 7,776,027 B2 | 8/2010 | Manna et al. | |
| 8,057,480 B2 | 11/2011 | Dorawa et al. | |
| 2002/0049464 A1 | 4/2002 | Donofrio et al. | |
| 2004/0115591 A1* | 6/2004 | Warner | 433/98 |
| 2004/0211260 A1* | 10/2004 | Girmonsky et al. | 73/579 |
| 2004/0267134 A1 | 12/2004 | Hossack et al. | |
| 2005/0288659 A1 | 12/2005 | Kimura et al. | |
| 2006/0229514 A1 | 10/2006 | Wiener | |
| 2006/0235424 A1 | 10/2006 | Vitale et al. | |
| 2007/0016235 A1 | 1/2007 | Tanaka et al. | |
| 2007/0031780 A1* | 2/2007 | Warner et al. | 433/101 |
| 2007/0083209 A1 | 4/2007 | Schenberger et al. | |
| 2007/0123769 A1 | 5/2007 | Fuller et al. | |
| 2007/0196784 A1* | 8/2007 | Bochi | A61B 17/1626 433/114 |
| 2008/0014627 A1 | 1/2008 | Merchant et al. | |
| 2008/0039845 A1* | 2/2008 | Bonutti et al. | 606/62 |
| 2008/0103515 A1* | 5/2008 | Wiener | 606/169 |
| 2009/0024161 A1* | 1/2009 | Bonutti | A61B 17/0401 606/213 |
| 2009/0036913 A1 | 2/2009 | Wiener et al. | |
| 2009/0098507 A1 | 4/2009 | Kirstgen | |
| 2009/0124585 A1 | 5/2009 | Cross et al. | |
| 2009/0222037 A1 | 9/2009 | Babaev et al. | |
| 2009/0275864 A1 | 11/2009 | Hirai | |
| 2010/0004585 A1 | 1/2010 | Boukhny et al. | |
| 2010/0004586 A1 | 1/2010 | Boukhny et al. | |
| 2010/0094321 A1 | 4/2010 | Akahoshi et al. | |
| 2010/0174336 A1 | 7/2010 | Stein | |
| 2015/0099966 A1 | 4/2015 | Young et al. | |

OTHER PUBLICATIONS

Non-Final Office Action dated Dec. 19, 2014 relating to U.S. Appl. No. 13/495,742, 26 pages.
Final Office Action dated Feb. 2, 2016 relating to U.S. Appl. No. 13/495,728, 9 pages.
Final Office Action dated Feb. 11, 2016 relating to U.S Appl. No. 13/495,742, 17 pages.
Non-Final Office Action dated Aug. 25, 2015 relating to U.S. Appl. No. 13/495,728, 13 pages.
Non-Final Office Action dated Apr. 28, 2015 relating to U.S. Appl. No. 13/495,742, 14 pages.
Non-Final Office Action dated Apr. 22, 2015 relating to U.S. Appl. No. 13/495,728, 17 pages.
Non-Final Office Action dated Aug. 25, 2015 relating to U.S. Appl. No. 13/495,728, 21 pages.
Non-Final Office Action from U.S. Appl. No. 13/495,728, Jul. 14, 2016, 10 pages.
Non-Final Office Action for U.S. Appl. No. 13/495,742, Aug. 25, 2016, 17 pages.

* cited by examiner

METHODS AND SYSTEMS FOR CONTROLLING AN ULTRASONIC HANDPIECE BASED ON SENSED PRESSURE

CROSS REFERENCE TO RELATED APPLICATIONS

This application claims priority to U.S. Provisional Patent Application No. 61/496,147 filed Jun. 13, 2011, U.S. Provisional Patent Application No. 61/526,182 filed Aug. 22, 2011, and U.S. Provisional Patent Application No. 61/526,207 filed Aug. 22, 2011, which are hereby incorporated by reference in their respective entireties.

BACKGROUND

The present disclosure relates generally to medical devices and, more particularly, to methods and systems for controlling a handpiece based on sensed pressure.

Various types of known medical procedures involve repair and stabilization of body tissue. Such medical procedures may be utilized, for example, to treat conditions, such as, without limitation, a defect, damage, or fracture to bone, damaged or torn muscle, ligament or tendon, or separation of body tissues, etc. For example, fractured bones often involve stabilization of the bone in order to promote healing. Different bones and/or different types of fractures generally require unique procedures and/or surgical implements to facilitate stabilization of the body tissue. Accordingly, medical personnel employ a variety of surgical implements, such as screws, plates, and rods, to stabilize the bone across the fracture. In another example, further surgical implements may be used to anchor torn ligaments or tendons to other appropriate body tissue. As such, a variety of medical procedures and surgical implements are known to be used within the body of a patient to facilitate repair, stabilization, and/or healing of body tissue.

BRIEF SUMMARY

In one aspect, a method is provided for controlling a handpiece. The method includes receiving a pressure signal from the handpiece. The pressure signal is indicative of a pressure between the handpiece and a surgical implement. The method further includes determining the pressure between the handpiece and the surgical implement, comparing the pressure to a predetermined pressure range, and transmitting a control signal to the handpiece when the pressure is within the predetermined pressure range.

In another aspect, a surgical generator is provided for use with a handpiece. The surgical generator includes a processing device, and a memory device having encoded thereon computer-readable instructions that are executable by the processing device to perform functions including receiving a pressure signal from the handpiece. The pressure signal is indicative of a pressure between the handpiece and a surgical implement. The functions further include determining the pressure between the handpiece and the surgical implement, comparing the pressure to a predetermined pressure range, and transmitting a control signal to the handpiece when the pressure is within the predetermined pressure range.

In yet another aspect, a system is provided. The system includes a handpiece configured to generate vibratory energy, and a generator coupled to the handpiece. The generator includes a processing device and a memory device having encoded thereon computer-readable instructions that are executable by the processing device to perform functions including receiving a pressure signal from the handpiece. The pressure signal is indicative of a pressure between the handpiece and a surgical implement. The functions further include determining the pressure between the handpiece and the surgical implement, comparing the pressure to a predetermined pressure range, and transmitting a control signal to the handpiece when the pressure is within the predetermined pressure range.

The features, functions, and advantages described herein may be achieved independently in various embodiments of the present disclosure or may be combined in yet other embodiments, further details of which may be seen with reference to the following description and drawings.

BRIEF DESCRIPTION OF THE DRAWINGS

FIG. 1 is a schematic illustration of an exemplary surgical system;

FIG. 2 is a cross-sectional view of an exemplary handpiece that may be used with the surgical system shown in FIG. 1;

FIG. 3 is a flowchart of an exemplary method of controlling the surgical system shown in FIG. 1; and FIG. 4 is a flowchart of another exemplary method of controlling the surgical system shown in FIG. 1.

Although specific features of various embodiments may be shown in some drawings and not in others, this is for convenience only. Any feature of any drawing may be referenced and/or claimed in combination with any feature of any other drawing.

DETAILED DESCRIPTION

The present disclosure relates generally to medical devices and, more particularly, to methods and systems for controlling handpieces based on sensed pressure. In one embodiment, a generator receives a pressure signal from a handpiece. The pressure signal is indicative of a pressure between the handpiece and a surgical implement. The pressure is compared to a predetermined pressure range, and a control signal is transmitted to the handpiece when the pressure is within the predetermined pressure range. The handpiece generates vibratory energy, which is transmitted to the surgical implement.

Exemplary technical effects of the methods and systems described herein may include at least one of (a) identifying a handpiece based on an identifier; (b) retrieving at least one setting for the handpiece based on the identifier; (c) determining whether the handpiece is in an active weld cycle; (d) receiving a pressure signal from the handpiece; (e) determining the pressure between the handpiece and a surgical implement; (f) comparing the pressure to a predetermined pressure range; (g) providing at least one indication associated with the pressure; (h) determining whether the pressure has settled within the predetermined pressure range for at least a predetermined settling interval; (i) determining whether a foot pedal is depressed; and (j) transmitting a control signal to the handpiece.

As used herein, an element or step recited in the singular and preceded with the word "a" or "an" should be understood as not excluding plural elements or steps unless such exclusion is explicitly recited. Moreover, references to "one embodiment" and/or the "exemplary embodiment" are not intended to be interpreted as excluding the existence of additional embodiments that also incorporate the recited features.

Figure 1:
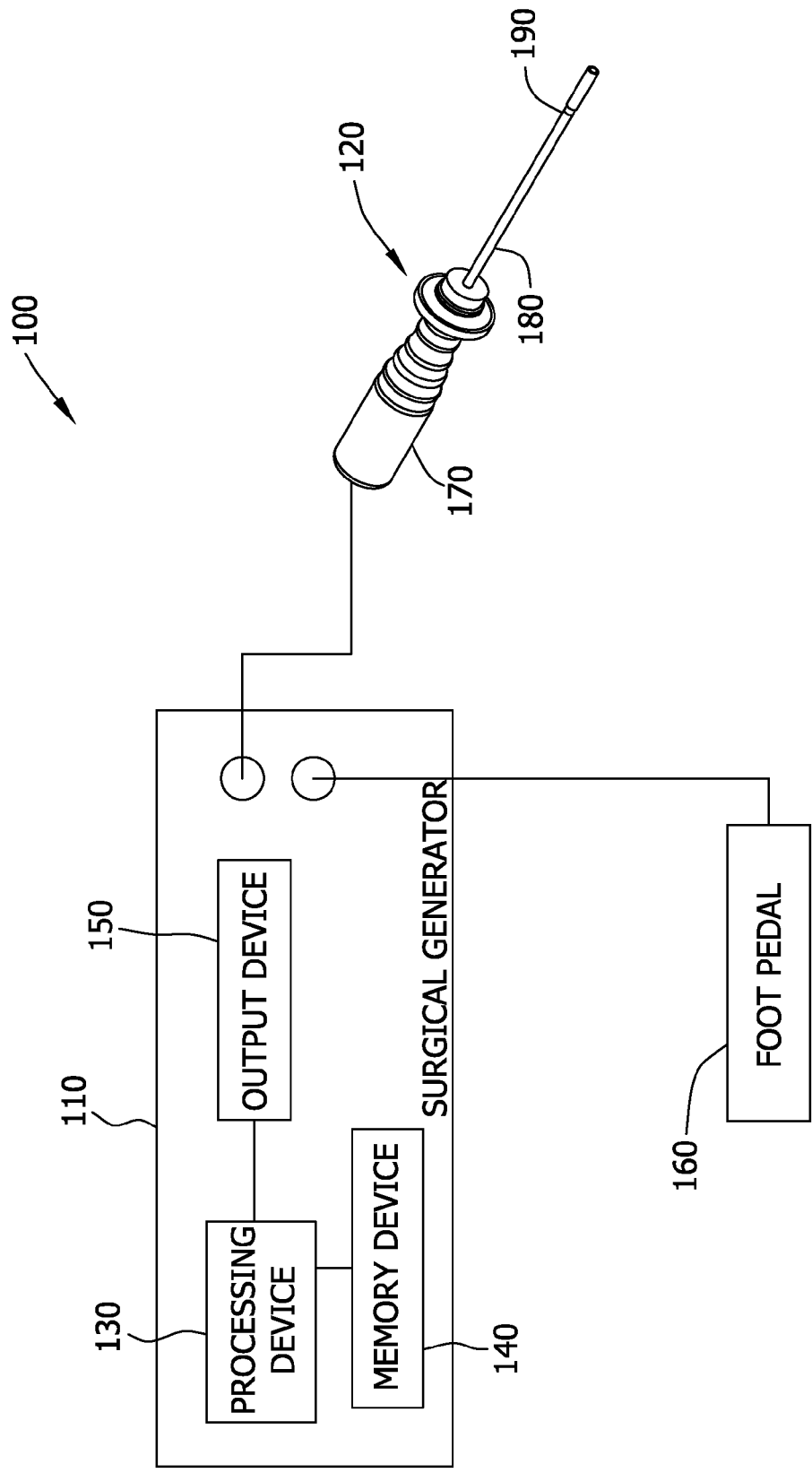
FIGS. 1-4 show exemplary embodiments of the methods and systems described herein.

FIG. 1 shows an exemplary surgical system 100 including a surgical generator 110 and a handpiece 120, which may be removably coupled to surgical generator 110. Alternatively, surgical generator 110 may be integrated with handpiece 120. As used herein, surgical and/or surgery are used to generally refer to any medical procedure involving a patient (a human being, an animal, etc.) and may include in-patient procedures, out-patient procedures, invasive procedures, non-invasive procedures, and/or minimally invasive procedures. In at least some embodiments, surgical implements (not shown) are disposed within the patient's body in orientations suitable for a respective medical procedure, such as a fracture stabilization procedure. Surgical implements may include implants or other suitable medical devices such as, without limitation, pins, screws, fasteners, dowels, rods, plates, and/or anchors. Moreover, as used herein, handpiece is used to generally refer to a housing, casing, frame, holder, and/or support that can be manually carried and manipulated during a medical procedure involving a patient.

In the exemplary embodiment, surgical generator 110 includes a processing device 130 and a memory device 140 coupled to processing device 130. Processing device 130 may include, without limitation, a microcontroller, a microprocessor, a programmable gate array, an application specific integrated circuit (ASIC), a logic circuit, and/or any other circuit, integrated or otherwise, suitable to perform as described herein. Memory device 140 includes one or more devices operable to enable information such as executable instructions and/or other data to be stored and/or retrieved. Memory device 140 may include one or more computer readable media including, without limitation, hard disk storage, optical drive/disk storage, removable disk storage, flash memory, non-volatile memory, ROM, electrically-erasable programmable read-only memory (EEPROM), and/or random access memory (RAM). Memory device 140 is used to store one or more of predetermined thresholds, resonant frequencies, settings specific to handpiece 120, and/or executable instructions.

In the exemplary embodiment, surgical generator 110 includes an output device 150 for example, a cathode ray tube (CRT), a liquid crystal display (LCD), an LED display, an "electronic ink" display, and/or other device suitable to display information to an operator. Additionally, output device 150 may include an audio output device (e.g., a speaker, etc.) to indicate verbal instructions, alerts, and/or warnings to the operator.

In the exemplary embodiment, surgical generator 110 includes one or more input devices, such as, without limitation, a button, a pedal, a knob, a keypad, a pointing device, a mouse, a touch sensitive panel (e.g., a touch pad or a touchscreen), a gyroscope, a position detector, and/or an audio input (e.g., a microphone). For example, in the exemplary embodiment, a foot pedal 160 is removably coupled to surgical generator 110 to enable an operator to provide input to surgical generator 110. In one embodiment, the input device is integrated with surgical generator 110. In another embodiment, the input device is remote from surgical generator 110 and coupled thereto.

Different types of handpieces 120 may be used with surgical generator 110 based on a type of medical procedure and/or a type of surgical implement. For example, various handpieces 120 may have different configurations and/or properties (e.g., acoustical characteristics, resonance frequency), and/or various surgical implements may require handpieces 120 of different sizes and/or configurations. In the exemplary embodiment, an identifier (not shown) enables surgical generator 110 to automatically identify handpiece 120. For example, surgical generator 110 may read and/or detect a resistance identification, an RFID tag, and/or another identifying component to differentiate handpiece 120 from other handpieces 120. Additionally or alternatively, an operator may manually identify handpiece 120. In at least some embodiments, the identifier is associated with multiple medical procedures and/or surgical implements. In such embodiments, the operator may provide, and surgical generator 110 may receive, one or more inputs to select a medical procedure to be performed and/or a surgical implement to be interfaced.

In this manner, one or more handpieces 120 may be replaced between medical procedures. In at least some embodiments, handpiece 120 is removed after each patient such that handpiece 120 may be autoclaved between medical procedures to substantially ensure sterility for one or more subsequent patients. Accordingly, handpiece 120 is configured to withstand multiple autoclave procedures.

In the exemplary embodiment, handpiece 120 includes an outer housing 170, a horn 180 extending longitudinally from outer housing 170, an end effector 190 coupled to horn 180, and a sheath 195 (shown in FIG. 2) coupled to outer housing 170 and extending about and spaced radially from horn 180 and/or end effector 190. In the exemplary embodiment, horn 180 and/or end effector 190 are sized and/or configured to slide within sheath 195. In at least some embodiments, end effector 190 is integrated with horn 180. In the exemplary embodiment, handpiece 120 is useable to affect one or multiple surgical implements during a surgery. More specifically, handpiece 120 applies vibratory energy, such as ultrasonic energy, to one or more of the surgical implements to form a weld between the surgical implements. Alternatively, handpiece 120 may apply any energy that enables surgical generator 110 and/or handpiece 120 to function as described herein.

In the exemplary embodiment, handpiece 120 is configured to provide an ergonomic interaction with an operator including, without limitation, a surgeon, a doctor, a surgery assistant, a nurse, a veterinarian, and/or other medical personnel present for a medical procedure. Other shapes and/or sizes of handpiece 120 may be included in other surgical system embodiments. In at least some embodiments, handpiece 120 is configured to interact with and/or be utilized by a robotic arm for robotic and/or remote control of handpiece 120.

Figure 2:
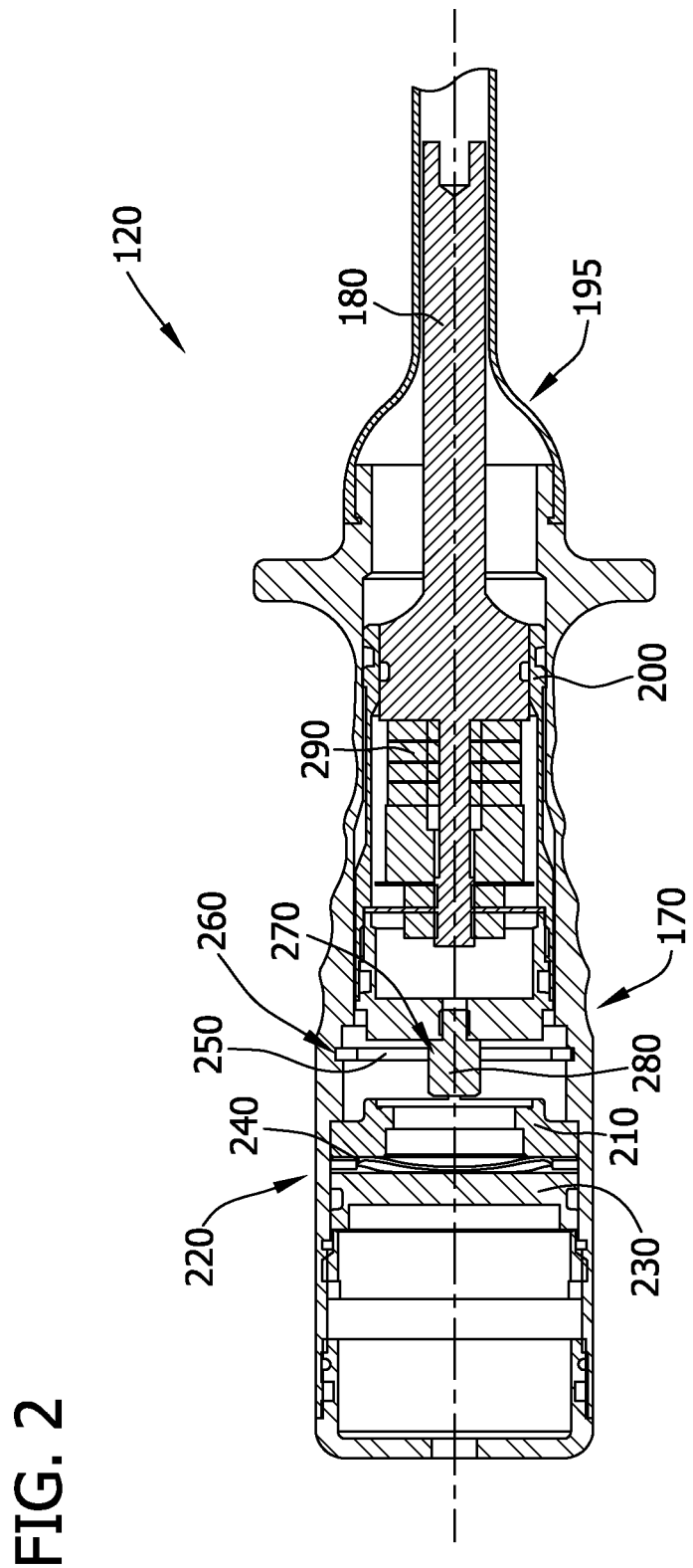

FIG. 2 is a cross-sectional view of handpiece 120. In the exemplary embodiment, outer housing 170 houses at least an inner housing 200 and at least a portion of a transducer system or, more specifically, load cell 210. In the exemplary embodiment, load cell 210 is configured to detect a first force and/or pressure applied to load cell 210 and transmit to surgical generator 110 (shown in FIG. 1) a pressure signal associated with and/or indicative of the first pressure. The first pressure is associated with a force and/or pressure between end effector 190 (shown in FIG. 1) and a surgical implement in contact with end effector 190, which, in turn, directly applies a force and/or pressure to horn 180.

In the exemplary embodiment, a biasing mechanism 220 is positioned within outer housing 170 to counteract, reduce and/or limit the first pressure applied to load cell 210. More specifically, biasing mechanism 220 is moveable between an unflexed or home position and a flexed position. As the first pressure applied to load cell 210 generally increases, in the exemplary embodiment, biasing mechanism 220 moves towards the flexed position. Conversely, as the first pressure applied to load cell 210 generally decreases, in the exemplary embodiment, biasing mechanism 220 moves towards the home position. In the exemplary embodiment, biasing mechanism 220 includes a spring plate 230 and a wave spring 240 that is configured to compress as the first pressure increases and/or expand as the first pressure decreases. Alternatively, any type of biasing mechanism 220 may be used that enables handpiece 120 to function as described herein.

In the exemplary embodiment, outer housing 170 defines a cavity therein that is sized and/or configured such that inner housing 200 is retained within outer housing 170. More specifically, outer housing 170 and/or inner housing 200 includes at least one retaining mechanism 250 that facilitates counteracting, reducing, and/or limiting the first pressure applied to load cell 210. For example, in the exemplary embodiment, retaining mechanism 250 is positioned within outer housing 170 between inner housing 200 and load cell 210 to prevent and/or limit inner housing 200 from moving towards load cell 210 beyond a predetermined position. In the exemplary embodiment, a portion of retaining mechanism 250 is positioned at the predetermined position within a groove 260 defined by an inner surface of outer housing 170. In the exemplary embodiment, retaining mechanism 250 includes an opening 270 extending longitudinally therethrough, and a standoff 280 coupled to inner housing 200 extends through opening 270 such that standoff 280 is configured to directly apply the first pressure to load cell 210. Alternatively, any type of retaining mechanism 250 may be used that enables handpiece 120 to function as described herein.

In the exemplary embodiment, inner housing 200 houses at least a portion of horn 180 and at least a portion of a transducer system or, more specifically, vibrating mechanism 290 coupled to horn 180. In the exemplary embodiment, vibrating mechanism 290 is a piezoelectric stack that is configured to generate vibratory energy (e.g., ultrasonic energy) upon receiving a control signal to activate a weld cycle. In the exemplary embodiment, horn 180 is configured to transmit the vibratory energy to an operative site. More specifically, horn 180 is coupleable to end effector 190 such that the vibratory energy is transmitted to end effector 190 through horn 180. Alternatively, the vibratory energy may be transmitted to the operative site using any mechanism that enables handpiece 120 to function as described herein.

The transducer system includes at least vibrating mechanism 290 and load cell 210. In this manner, the transducer system is configured to detect the first pressure, transmit the pressure signal, and generate ultrasonic vibratory energy. In the exemplary embodiment, vibrating mechanism 290 is remote from load cell 210. Alternatively, vibrating mechanism 290 may be adjacent and/or integrated with load cell 210.

In at least some embodiments, handpiece 120 includes a series of electrical contacts that are coupled to vibrating mechanism 290. In such embodiments, the electrical contacts are moveable between a closed configuration and an open configuration such that the electrical contacts are electrically and/or communicatively coupled and/or decoupled, respectively. In such embodiments, as pressure applied to end effector 190, horn 180, and/or load cell 210 generally increases, the electrical contacts move toward the closed configuration, thereby coupling surgical generator 110 to vibrating mechanism 290. Conversely, as pressure applied to end effector 190, horn 180, and/or load cell 210 generally decreases, in such embodiments, the electrical contacts move toward the open configuration, thereby decoupling surgical generator 110 from vibrating mechanism 290. Alternatively, the electrical contacts may be positioned anywhere within handpiece 120 that enables surgical system 100 to function as described herein.

Figure 3:
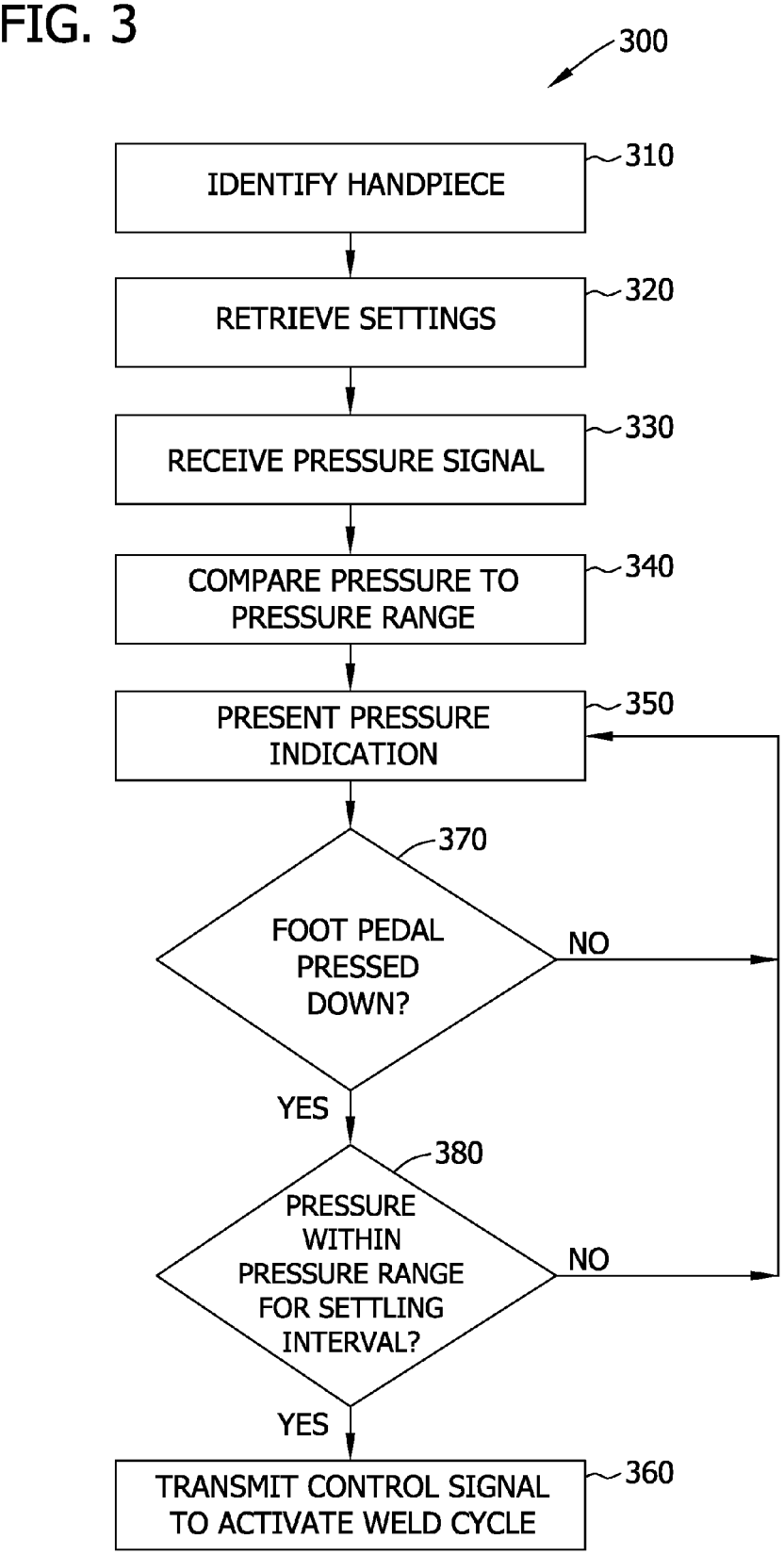

FIG. 3 is a flowchart of an exemplary method 300 of controlling surgical system 100. During operation, in the exemplary embodiment, handpiece 120 is identified 310 based on an identifier and/or selected based on a type of medical procedure and/or surgical implement. In the exemplary embodiment, surgical generator 110 retrieves 320 one or more settings associated with handpiece 120, the medical procedure, and/or the surgical implement from memory device 140 based on the identifier. The settings are used by surgical generator 110 to provide one or more control signals to handpiece 120. Settings retrieved from memory device 140 may include, without limitation, frequencies, voltages, currents, and/or control algorithms. For example, in the exemplary embodiment, the setting retrieved from memory device 140 includes a predetermined first force and/or pressure range that enables vibratory energy transfer to the surgical implement, as described below.

Upon identification 310 and/or selection of handpiece 120 and retrieval 320 of one or more settings from memory device 140, surgical system 100 is generally ready to affect the surgical implement. In the exemplary embodiment, end effector 190 is positioned at least partially within the patient and in contact with the surgical implement. More specifically, the operator uses handpiece 120 to apply force and/or pressure to the surgical implement, which, in turn, applies a force and/or pressure to horn 180 and inner housing 200. As a result, standoff 280 applies the first pressure to load cell 210, which detects the first pressure and transmits the pressure signal from handpiece 120 to surgical generator 110.

In the exemplary embodiment, surgical generator 110 receives 330 the pressure signal from handpiece 120 and compares 340 the pressure between end effector 180 and the surgical implement, as indicated by the pressure signal, to the first pressure range. More specifically, surgical generator 110 determines a pressure based on the pressure signal, and the pressure is compared to the pressure range. When the pressure is outside of the first pressure range, surgical generator 110 does not transmit a control signal to activate a weld cycle, thereby inhibiting welding when undesirable pressure is applied. In the exemplary embodiment, the pressure is within the first pressure range when the axial force applied to handpiece 120 is between approximately 30 newtons (N) and approximately 38 N. Alternatively, the first pressure range may be associated with any force that enables handpiece 120 to function as described herein.

In at least some embodiments, output device 150 presents and/or provides 350 an indication of the pressure to the operator. For example, in one embodiment, a visual display provides 350 a visual indication of the applied pressure relative to the first pressure range such that the operator is able to visualize what, if any, corrections need to be made in order to provide a pressure within the first pressure range. Additionally or alternatively, an audio output device provides 350 an audible tone indicative of the applied pressure, and/or a tactile output device provides 350 vibrations indicative of the applied pressure. The tone and/or vibrations may include three rates, volumes, and/or intensities: a first rate, volume, and/or intensity indicating the pressure is below the first pressure range, a second rate, volume, and/or intensity indicating the pressure is within the first pressure range, and a third rate, volume, and/or intensity indicating the pressure is above the first pressure range. As such, the audible tone and/or the vibrations enable the operator to understand the applied pressure relative to the first pressure range without diverting the operator's visual attention from the patient and/or surgical implement.

In the exemplary embodiment, when the pressure is below the first pressure range, output device 150 provides 350 no visual or audible indicator. When the pressure is within the first pressure range, output device 150 provides 350 a ready light and a beep that is emitted at one second intervals. When the pressure is above the first pressure range, output device 150 provides 350 an "over pressure" display and a beep that is emitted at half-second intervals. Alternatively, output device 150 may provide any indication to the operator that enables surgical system 100 to function as described herein.

In the exemplary embodiment, when the applied pressure is within the first pressure range, the operator presses foot pedal 160 down to initiate transmission of the control signal to activate a weld cycle. More specifically, surgical generator 110 transmits 360 the control signal to handpiece 120 upon determining and/or identifying that the applied pressure is within the first pressure range and/or determining and/or identifying 370 that foot pedal 160 is depressed. In one embodiment, the control signal is transmitted 360 to handpiece 120 upon receiving the first indication that the applied pressure is within the first pressure range and then receiving the second indication that foot pedal 160 is depressed. In another embodiment, the control signal is transmitted 360 to handpiece 120 upon receiving the second indication that foot pedal 160 is depressed and then receiving the first indication that the applied pressure is within the first pressure range.

In at least some embodiments, surgical generator 110 requires that the applied pressure settle within the first pressure range for a predetermined settling interval. More specifically, surgical generator 110 determines and/or identifies 380 whether the applied pressure has settled within the first pressure range for a duration that is at least equal to the settling interval. As used herein, settling is used herein to generally refer to stabilizing and/or staying within a range. The settling interval encourages the operator to provide a consistent pressure within the first pressure range prior to transmitting the control signal to activate a weld cycle. In this manner, the settling interval enables consistent and proper welding to be provided between surgical implements, as compared to known surgical systems. In the exemplary embodiment, the settling interval is approximately 2.0 seconds. Alternatively, surgical generator 110 may utilize any settling interval that enables surgical system 100 to function as described herein.

In the exemplary embodiment, vibrating mechanism 290 receives the control signal to activate a weld cycle and generates vibratory energy upon receiving the control signal. The vibratory energy is transferred through horn 180 and end effector 190 to the surgical implement. The vibratory energy propagates through the surgical implement to vibrate the surgical implement and an adjacent surgical implement, which generates heat and a weld therebetween.

Figure 4:
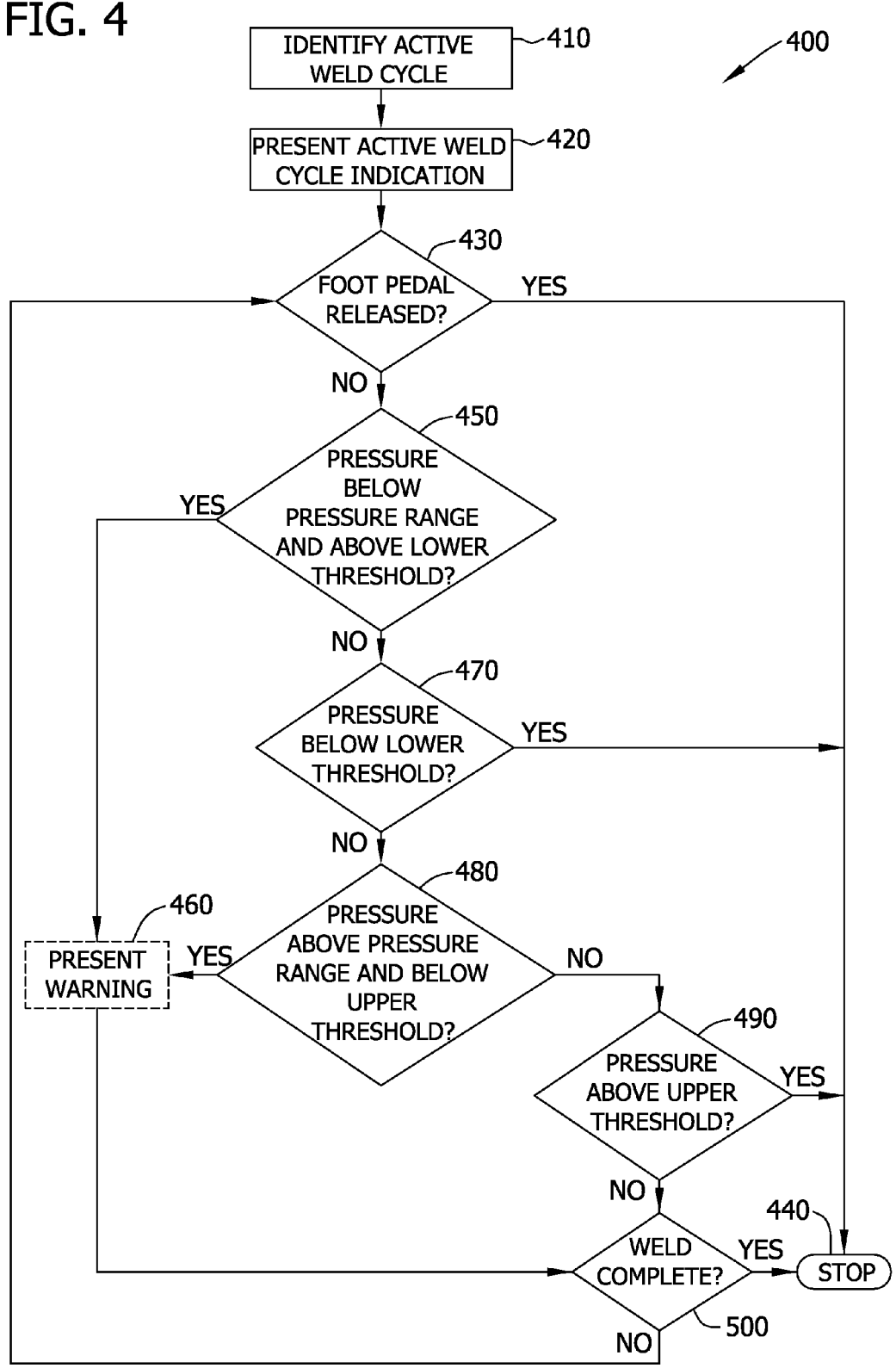

FIG. 4 is a flowchart of an exemplary method 400 of controlling surgical system 100 during an active weld cycle. In the exemplary embodiment, surgical generator 110 determines and/or identifies 410 that surgical system 100 is in the active weld cycle. During operation of handpiece 120 in the active weld cycle, output device 150 provides 420 an indication of the active weld cycle to the operator. For example, in one embodiment, an audio output device provides 390 an audible tone indicative of the active weld cycle. In the exemplary embodiment, when foot pedal 160 is released during the active weld cycle, surgical generator 110 determines and/or identifies 430 that foot pedal 160 is released and stops 440 transmission of the control signal and/or transmits a second control signal to stop the active weld cycle.

When surgical generator 110 determines and/or identifies 450 that the applied pressure is below a predetermined second pressure range and above a predetermined lower threshold during the active weld cycle, output device 140 may provide 460 a warning during and/or at the end of the weld cycle. When surgical generator 110 determines and/or identifies 470 that the applied pressure is at or below the lower threshold during the active weld cycle a stop state, surgical generator 110 may stop 440 transmission of the control signal and/or transmit a second control signal to stop the active weld cycle. In the exemplary embodiment, the applied pressure is within the second pressure range when the axial force applied to handpiece 120 is between approximately 0 N and approximately 50 N, and the lower threshold is approximately 0 N. In this manner, surgical generator 110 stops 440 transmission of the control signal and/or transmits a second control signal to stop the active weld cycle when the applied pressure is below the second pressure range in the exemplary embodiment. Alternatively, the second pressure range and/or the lower threshold may be associated with any force that enables handpiece 120 to function as described herein.

Moreover, when surgical generator 110 determines and/or identifies 480 that the applied pressure is above the second pressure range and below a predetermined upper threshold during the active weld cycle, output device 140 may provide 460 a warning during and/or at the end of the weld cycle. When surgical generator 110 determines and/or identifies 490 that the applied pressure is at or above the upper threshold during the active weld cycle, surgical generator 110 stops 440 stops transmission of the control signal and/or transmits a second control signal to stop the active weld cycle. In the exemplary embodiment, the applied pressure is within the second pressure range when the axial force applied to handpiece 120 is between approximately 0 N and approximately 50 N, and the upper threshold is undefined (i.e., surgical generator 110 does not recognize an upper threshold in the exemplary embodiment). In this manner, surgical generator 110 provides 460 a warning during and/or at the end of the weld cycle when the applied pressure is above the second pressure range in the exemplary embodiment. Alternatively, the second pressure range and/or the upper threshold may be associated with any force that enables handpiece 120 to function as described herein.

In the exemplary embodiment, the active weld cycle stops when the weld is complete. More specifically, surgical generator 110 determines and/or identifies 500 that the weld is complete based on a predetermined amount of energy or work applied by handpiece 120, and stops 440 transmission of the control signal and/or transmits a second control signal to stop the active weld cycle when the weld is complete. In the exemplary embodiment, the amount of energy applied to the surgical implement is approximately 100 Joules (J). Alternatively, surgical generator 110 may apply any amount of energy that enables surgical system 100 to function as described herein.

The embodiments described herein relate generally to medical devices and, more particularly, to methods and systems for controlling a handpiece based on sensed pressure. The embodiments described herein monitor forces and/or pressures applied to a handpiece, its components, and/or a surgical implement. As such, the embodiments described herein facilitate creating effective and/or reliable welds, thereby improving a repair, stabilization, and/or healing time associated with the patient.

Exemplary embodiments of handpieces are described above in detail. The methods and systems are not limited to the specific embodiments described herein, but rather, components of systems and/or steps of the method may be utilized independently and separately from other components and/or steps described herein. Each method step and each component may also be used in combination with other method steps and/or components. Although specific features of various embodiments may be shown in some drawings and not in others, this is for convenience only. Any feature of a drawing may be referenced and/or claimed in combination with any feature of any other drawing.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of controlling a handpiece, said method comprising:
   receiving a pressure signal from the handpiece, the pressure signal indicative of a manually applied pressure generated by a user of the handpiece between the handpiece and the surgical implement by pressing the handpiece against the surgical implement;
   determining the pressure between the handpiece and the surgical implement;
   comparing the pressure to a predetermined pressure range;
   transmitting a signal to the handpiece causing the handpiece to transmit vibratory energy to the surgical implement to form a weld to stabilize body tissue with the weld when the determined pressure is within the predetermined pressure range indicating the manually applied pressure between the handpiece and the surgical implement is suitable for forming the weld; and
   determining whether the pressure has settled within the predetermined pressure range for at least a predetermined settling interval, wherein transmitting the signal further comprises transmitting the signal to the handpiece when the pressure has settled within the predetermined pressure range for at least the predetermined settling interval, wherein the predetermined settling interval is 2 seconds.

2. The method in accordance with claim 1 further comprising:
   identifying the handpiece based on an identifier, the identifier being associated with at least one of multiple procedures and surgical implements; and
   retrieving at least one setting for the handpiece based on the identifier.

3. The method in accordance with claim 1 further comprising providing at least one indication associated with the pressure.

4. The method in accordance with claim 1 further comprising:
   providing a first indication when the pressure is below the predetermined pressure range;
   providing a second indication when the pressure is within the predetermined range; and
   providing a third indication when the pressure is above the predetermined pressure range.

5. The method in accordance with claim 1 further comprising determining whether a foot pedal is depressed, wherein transmitting the signal further comprises transmitting the signal to the handpiece when the pressure is within the predetermined pressure range and the foot pedal is depressed.

6. The method in accordance with claim 1 further comprising determining whether the handpiece is in an active weld cycle.

7. A surgical generator for use with a handpiece, said surgical generator comprising:
   a processor; and
   a memory device having encoded thereon computer-readable instructions that are executable by the processor to perform functions comprising:
   receiving a pressure signal from the handpiece, the pressure signal indicative of a manually applied pressure generated by a user of the handpiece between the handpiece and a surgical implement by pressing the handpiece against the surgical implement;
   determining the pressure between the handpiece and the surgical implement;
   comparing the pressure to a predetermined pressure range;
   transmitting a signal to the handpiece causing the handpiece to transmit vibratory energy to the surgical implement to form a weld to stabilize body tissue with the weld when the determined pressure is within the predetermined pressure range indicating the manually applied pressure between the handpiece and the surgical implement is suitable for forming the weld;
   determining whether the pressure has settled within the predetermined pressure range for at least a predetermined settling interval; and
   transmitting the signal to the handpiece when the pressure has settled within the predetermined pressure range for at least the predetermined settling interval, wherein the predetermined settling interval is 2 seconds.

8. The surgical generator in accordance with claim 7, wherein the functions performed by the processor further comprise:
   identifying the handpiece based on an identifier, the identifier being associated with at least one of multiple procedures and surgical implements; and
   retrieving at least one setting for the handpiece based on the identifier.

9. The surgical generator in accordance with claim 7, wherein the functions performed by the processor further comprise providing at least one indication associated with the pressure.

10. The surgical generator in accordance with claim 7, wherein the functions performed by the processor further comprise:
    providing a first indication when the pressure is below the predetermined pressure range;
    providing a second indication when the pressure is within the predetermined range; and
    providing a third indication when the pressure is above the predetermined pressure range.

11. The surgical generator in accordance with claim 7, wherein the functions performed by the processor further comprise:
  determining whether a foot pedal is depressed; and
  transmitting the signal to the handpiece when the pressure is within the predetermined pressure range and the foot pedal is depressed.

12. The surgical generator in accordance with claim 7, wherein the functions performed by the processor further comprise determining whether the handpiece is in an active weld cycle.

13. A system comprising:
  a handpiece configured to generate vibratory energy; and
  a generator coupled to the handpiece, the generator comprising a processor and a memory device having encoded thereon computer-readable instructions that are executable by the processor to perform functions comprising:
  receiving a pressure signal from the handpiece, the pressure signal indicative of a manually applied pressure generated by a user of the handpiece between the handpiece and a surgical implement by pressing the handpiece against the surgical implement;
  determining the pressure between the handpiece and the surgical implement;
  comparing the pressure to a predetermined pressure range;
  transmitting a signal to the handpiece causing the handpiece to transmit the vibratory energy to the surgical implement to form a weld to stabilize body tissue with the weld when the determined pressure is within the predetermined pressure range indicating the manually applied pressure between the handpiece and the surgical implement is suitable for forming the weld;
  determining whether the pressure has settled within the predetermined pressure range for at least a predetermined settling interval; and
  transmitting the signal to the handpiece when the pressure has settled within the predetermined pressure range for at least the predetermined settling interval, wherein the predetermined settling interval is 2 seconds.

14. The system in accordance with claim 13, wherein the functions performed by the processor further comprise:
  identifying the handpiece based on an identifier, the identifier being associated with at least one of multiple procedures and surgical implements; and
  retrieving at least one setting for the handpiece based on the identifier.

15. The system in accordance with claim 13, wherein the functions performed by the processor further comprise providing at least one indication associated with the pressure.

16. The system in accordance with claim 13, wherein the functions performed by the processor further comprise:
  determining whether a foot pedal is depressed; and
  transmitting the signal to the handpiece when the pressure is within the predetermined pressure range and the foot pedal is depressed.

17. The system in accordance with claim 13, wherein the functions performed by the processor further comprise determining whether the handpiece is in an active weld cycle.

* * * * *